United States Patent [19]

Bajwa et al.

[11] 4,134,986

[45] Jan. 16, 1979

[54] POLYOXYGENATED LABDANE DERIVATIVES

[75] Inventors: Balbir S. Bajwa, Bombay; Sujata V. Bhat, Thana; Horst Dornauer; Noel J. de Souza, both of Bombay, all of India

[73] Assignee: Hoechst Aktiengesellschaft, Frankfurt am Main, Germany

[21] Appl. No.: 787,961

[22] Filed: Apr. 15, 1977

[30] Foreign Application Priority Data

Dec. 3, 1976 [DE] Fed. Rep. of Germany ....... 2654796

[51] Int. Cl.² .................... A61K 31/35; C07D 311/74
[52] U.S. Cl. ................................. 424/283; 260/345.2
[58] Field of Search ...................... 260/345.2; 424/283

[56] References Cited

U.S. PATENT DOCUMENTS 3,631,039  12/1971  Andrews et al. ................. 260/345.2

Primary Examiner—Nicky Chan
Attorney, Agent, or Firm—Curtis, Morris & Safford

[57] ABSTRACT

The invention relates to novel polyoxygenated labdane derivatives and to a process for preparing same. The polyoxygenated labdane derivatives of the invention are characterized by valuable pharmacological properties, for example a hypotensive effect and a positive inotropic activity.

7 Claims, No Drawings

POLYOXYGENATED LABDANE DERIVATIVES

This invention relates to novel polyoxygenated labdane derivatives and to a process for preparing same. The polyoxygenated labdane derivatives of the invention are characterized by valuable pharmacological properties, for example a hypotensive effect and a positive inotropic activity.

More particularly, the present invention provides polyoxygenated labdane derivatives of the formula I

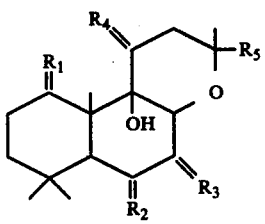

in which
$R_1$, $R_2$, $R_3$ and $R_4$, which may be identical or different represent oxygen or the group

$R_6$ being hydrogen, alkyl, alkenyl or alkynyl having from 1 to 6 carbon atoms, cycloalkyl having from 5 to 8 carbon atoms, dialkylaminoalkyl or aralkyl in which the alkyl groups have at most 4 carbon atoms, acyl having from 1 to 20 carbon atoms, alkoxycarbonyl or arylaminocarbonyl having from 2 to 10 carbon atoms, and $R_5$ represents an ethyl or vinyl group.

In the case of derivatives carrying basic groups the acid addition salts are also an object of the invention.

It is obvious that the aforesaid definition of the polyoxygenated labdane derivatives is intended to include all possible stereoisomers and mixtures thereof.

Suitable alkyl, alkenyl or alkynyl groups for $R_6$ are methyl, allyl and propynyl, while a suitable cycloalkyl group for $R_6$ is cyclohexyl.

When $R_6$ stands for a dialkylaminoalkyl group, the diethylaminoethyl group may be mentioned and a suitable acid addition salt is, for example, one derived from an inorganic or organic acid, for example the hydrochloride, hydrobromide, sulfate, phosphate, acetate, oxalate, tartrate, citrate, maleate or fumarate.

Suitable aralkyl groups for $R_6$ are phenylalkyl groups, for example the benzyl group optionally carrying one or several substituents in the phenyl radical, for example halogen atoms such as fluorine, chlorine or bromine, alkyl and alkoxy groups having at most 3 carbon atoms, for example methyl, ethyl, methoxy and ethoxy, haloalkyl groups, for example trifluoromethyl, or nitro, amino and hydroxy groups.

A suitable acyl group for $R_6$ is an alkanoyl, alkenoyl, alkynoyl, aroyl, aralkanoyl or heteroaroyl group having up to 10 carbon atoms and at most 3 heteroatoms, for example oxygen, nitrogen or sulfur. There are mentioned by way of example alkanoyl groups such as formyl, acetyl, trifluoroacetyl, propionyl, butyryl, isobutyryl, valeryl, palmitoyl, stearoyl and bromoisobutyryl. The alkanoyl group can also be derived from a dicarboxylic acid, for example oxalic acid or succinic acid.

The alkenoyl groups may contain one or several double bonds, for example acryloyl, and oleoyl. The alkynoyl groups may contain one or several triple bonds, for example propiolyl, and additionally one or several double bonds. Suitable aroyl groups are especially the benzoyl group, the phenyl radical of which may be substituted by one or several substituents as defined above, for example alkyl, alkoxy, nitro, trifluoromethyl, or halogen. Examples of aralkanoyl or hetero-aroyl are the phenylacetyl and pyridine-3-carbonyl group.

Suitable examples of $R_6$ when it stands for an alkoxycarbonyl or arylaminocarbonyl radical are ethoxycarbonyl and anilinocarbonyl.

Preferred representatives of compounds of formula I are those in which $R_5$ stands for $-CH=CH_2$ or $-CH_2CH_3$, $R_1$, $R_2$ and $R_3$ are

and $R_4$ represents oxygen, or $R_1$ and $R_4$ represent oxygen and $R_2$ and $R_3$ are

or $R_1$, $R_2$ and $R_4$ represent oxygen and $R_3$ is

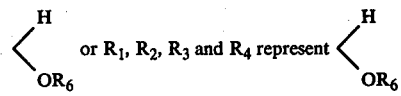

wherein the radicals

have the meanings specified above.

Especially preferred are compounds of formula I in which $R_5$ stands for $-CH=CH_2$ or $-CH_2CH_3$, $R_1$ is

$R_4$ represents oxygen or

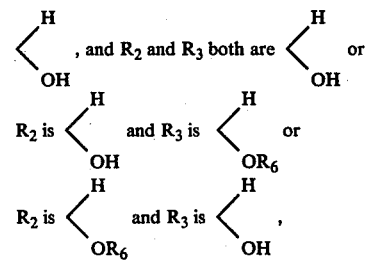

$R_6$ being an acyl radical as defined above. There are mentioned particularly compounds 1, 9, 10, 25, and 29 listed in the following Table.

In the following Table novel polyoxygenated labdane derivatives of formula I are listed together with their melting points. They were prepared by the methods described in the examples, in the last column the number of the respective example being indicated. Compounds IIa and IIb listed at the end of the table are suitable starting materials for the compounds of the invention and can also be prepared by the described processes from appropriate starting materials.

Table I

| Compound No. | $R_1$ | $R_2$ | $R_3$ | $R_4$ | $R_5$ | melt. point (° C) | Example No |
|---|---|---|---|---|---|---|---|
| 1 | H, OH | H, OH | H, OH | O | CH:CH$_2$ | 176–178 | 1 |
| 2 | H, OCH$_2$C$_6$H$_5$ | H, OH | H, OH | O | CH:CH$_2$ | 80–85 | 1 |
| 3 | H, OH | H, OCOCH$_3$ | H, OCH$_3$ | O | CH:CH$_2$ | 195–197 | 2 |
| 4 | H, OH | H, OH | H, OCH$_3$ | O | CH:CH$_2$ | not defined | 2 |
| 5 | H, OCH$_3$ | H, OH | H, OCOCH$_3$ | O | CH:CH$_2$ | 174–176 | 2 |
| 6 | H, OCH$_3$ | H, OH | H, OCOCH$_3$ | O | CH:CH$_2$ | 132–134 | 3 |
| 7 | H, OCH$_2$C$_6$H$_5$ | H, OH | H, OCOCH$_3$ | O | CH:CH$_2$ | 138–140 | 3 |
| 8 | H, OH | H, OCOCH$_3$ | H, O(CH$_2$)$_2$NEt$_2$ | O | CH:CH$_2$ | not defined | 3 |
| 9 | H, OH | H, OCOCH$_3$ | H, O(CH$_2$)$_2$NEt$_2$.HCl | O | CH:CH$_2$ | 255–257 | 3 |
| 10 | H, OH | H, OH | H, OCHO | O | CH:CH$_2$ | 297–299 | 4 |
| 11 | H, OH | H, OCOCH$_3$ | H, OCOCH$_3$ | H, OH | CH:CH$_2$ | 275–279 | 4 |
| 12 | H, OH | H, OH | H, OCOCH$_3$ | O | CH:CH$_2$ | 175–176 | 4 |
| 13 | H, OH | H, OH | H, OCOCH$_2$CH$_3$ | O | CH:CH$_2$ | 229–231 | 4 |
| 14 | H, OH | H, OCOCH$_3$ | H, OCOCH$_2$CH$_3$ | O | CH:CH$_2$ | 176–177 | 4 |
| 15 | H, OH | H, OH | H, OCO(CH$_2$)$_2$CH$_3$ | O | CH:CH$_2$ | 196–198 | 4 |
| 16 | H, OH | H, OCOCH$_3$ | H, OCO(CH$_2$)$_2$CH$_3$ | O | CH:CH$_2$ | 158–160 | 4 |
| 17 | H, OCH$_2$C$_6$H$_5$ | H, OH | H, OCOC(Br)(CH$_3$)$_2$ | O | CH:CH$_2$ | 203–206 | 4 |
| 18 | H, OCOCH$_3$ | H, OH | H, OCOCH$_3$ | O | CH:CH$_2$ | 217–218 | 4 |
| 19 | H, OCOCH$_3$ | H, OCOCH$_3$ | H, OCOCH$_3$ | O | CH:CH$_2$ | 178–180 | 4 |
| 20 | H, OCOC$_6$H$_5$, OCOC$_6$H$_5$ | H, OH, OH | H, OCOCH$_3$, OCOC$_6$H$_5$ | O | CH:CH$_2$ | 118–120 | 4 |

Table I-continued

| Compound No. | R$_1$ | R$_2$ | R$_3$ | R$_4$ | R$_5$ | melt. point (° C) | Example No |
|---|---|---|---|---|---|---|---|
| 21 | H, OH | H, OH | H, OCOOC$_2$H$_5$ | O | CH:CH$_2$ | 166–167 | 5 |
| 22 | H, OH | H, OCOCH$_3$ | H, OCOOC$_2$H$_5$ | O | CH:CH$_2$ | 177–179 | 5 |
| 23 | H, OCONHC$_6$H$_5$ | H, OH | H, OCOCH$_3$ | O | CH:CH$_2$ | 212–216 | 6 |
| 24 | H, OCONHC$_6$H$_5$ | H, OH | H, OCONHC$_6$H$_5$ | O | CH:CH$_2$ | 238–242 | 6 |
| 25 | H, OH | H, OCOCH$_2$CH$_3$ | H, OH | O | CH:CH$_2$ | 187–192 | 7 |
| 26 | O | H, OH | H, OCOCH$_3$ | O | CH$_2$CH$_3$ | 228–233 | 8 |
| 27 | O | O | H, OCOCH$_3$ | O | CH$_2$CH$_3$ | 163–165 | 9 |
| 28 | H, OH | H, OH | H, OH | H, OH | CH:CH$_2$ | 204–209 | 10 |
| 29 | H, OH | H, OH | H, OCOCH$_3$ | O | CH$_2$CH$_3$ | 245–248 | 11 |
| IIa | H, OH | H, OH | H, OCOCH$_3$ | O | CH:CH$_2$ | 228–232 | 4 |
| IIb | H, OH | H, OCOCH$_3$ | H, OH | O | CH:CH$_2$ | 207–211 | 7 |

It is another object of the present invention to provide a process for preparing the polyoxygenated labdane derivatives of formula I. As starting compounds there are used compounds of the following formula II

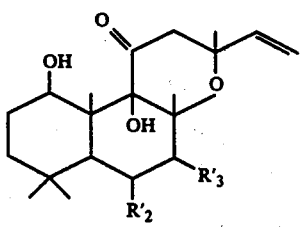

(II)

(cf. the last two compounds of the foregoing table) in which in the case of compound II a R'$_2$ is hydroxy and R'$_3$ is O-acyl and in the case of formula II b R'$_2$ os O-acyl and R'$_3$ is hydroxy.

A compound having a melting point of 228°–230° C., to which the structure IIa has been assigned, is obtained by extracting *Coleus forskohlii*, a plant of the Labiatae family, with a halogenated hydrocarbon solvent, for example one having 1 to 3 carbon atoms and up to 6 halogen atoms, removing the solvent from the extract to leave a residue, dissolving the residue in an alkanol, for example one having 1 to 6 carbon atoms, removing undissolved material from the alkanolic solution, and isolating said compound from the alkanolic solution, for example by evaporation of the alkanol. If desired, the plant may be priorly extracted with a hydrocarbon solvent and the isolated compound may be purified further by column chromatography and crystallization.

A compound having a melting point of 208°–211° C., to which the structure IIb has been assigned, is obtained by extracting *Coleus forskohlii* with a solvent such as aromatic hydrocarbons, aromatic and aliphatic halogenated hydrocarbons, dialkyl ethers, dialkyl ketones, alkanols, carboxylic acids and their esters, dimethylformamide, dioxane, tetrahydrofurane, and dimethylsulfoxide. The extract is then concentrated to a residue. The residue is treated in one of a number of ways, described below in more detail, with a solvent or solvent mixture to obtain a crude product which in turn is treated with a base, for example with an alkali alkoxide in a solvent such as an ether. On acidification to a pH of 5–7, concentration, and dilution with water, a mixture of crude terpenoids is filtered off. Other basic treatments involve an alkali carbonate or bicarbonate in an alcohol or aqueous alcohol, or a basic metal oxide such as basic aluminum oxide in a solvent such as an aromatic hydrocarbon or an ether, in each case with formation of a crude terpenoid product. This crude product can be chromatographed to obtain a semi-pure terpenoid. The crude terpenoid product can be recrystallized prior to chromatography, or the semi-pure terpenoid can be recrystallized after chromatography, from solvents such as ethyl acetate, chloroform or benzene, optionally in admixture with an aliphatic hydrocarbon having 5–7 carbon atoms, or preferably from petroleum ether, hexane, or pentane, to obtain the product, Coleforsin.

If an aromatic hydrocarbon such as benzene or toluene, or an aliphatic halohydrocarbon such as chloroform, is used as an extractant for the plant material, the crude product is obtained from the resulting residue by repeated solution and precipitation by addition of a material in which the residue is partly or entirely insoluble.

In an alternative process, the residue obtained by extraction of the plant with an aromatic hydrocarbon or a halohydrocarbon is first extracted with several portions of a lower alkanol having 1 to 6 carbon atoms. The alkanol extracts are combined, filtered and evaporated to dryness. This residue is then recrystallized as described above to form the crude product.

In a third embodiment, the residue obtained from the first extraction is further extracted with an alkanol and this extract is distributed between two immiscible solvents, for example benzene and water, in only one of which the desired material is soluble. The organic layer is separated, dried, and evaporated to form a residue which is then recrystallized as described above.

It is another object of the present invention to provide compounds of the formula III

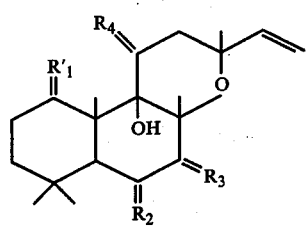

(III)

in which $R_1$, $R_2$ and $R_4$ are oxygen or

$R_6$ being hydrogen, alkyl, alkenyl, alkynyl, cycloalkyl, dialkylaminoalkyl, or aralkyl, and $R_3$ represents

Compounds of this type are prepared by subjecting to an acid or basic hydrolysis the compound of formula II a or other compounds of formula III in which $R_1$, $R_2$ and $R_4$ have the aforesaid meaning and $R_3$ stands for

wherein $R_6$ is acyl, alkoxycarbonyl or arylaminocarbonyl. For hydrolysis an inorganic acid, for example hydrochloric acid, or organic acid, for example trifluoroacetic acid, an alkali metal hydroxide, for example sodium hydroxide, or an alkali metal carbonate, for example potassium carbonate, can be used.

The reaction can be carried out in the presence of a solvent, for example an aqueous alkanol having at most 6 carbon atoms, for example methanol or ethanol, or a mixture of water with an ether miscible therewith, for example dioxane or tetrahydrofuran. The reaction can be accelerated or completed by heating up to the boiling temperature of the solvent used.

Compounds of formula III in which $R_1$, $R_3$ and $R_4$ are oxygen or

$R_6$ being hydrogen or alkyl, alkenyl, alkynyl, cycloalkyl, dialkylaminoalkyl, or aralkyl, can be prepared in analogous manner from the compound of formula II b or corresponding compounds of formula III in which $R_1$, $R_3$, and $R_4$ have the above meaning and $R_2$ stands for

wherein $R_6$ represents acyl, alkoxycarbonyl or arylaminocarbonyl.

It is another object of the present invention to provide a process for preparing compounds of formula III in which $R_1$, $R_2$ and $R_4$ have the aforesaid meaning and $R_3$ stands for

wherein $R_7$ has the meaning defined below, which comprises reacting a compound of formula II b or III in which $R_1$, $R_2$, and $R_4$ are oxygen or

$R_6$ having the aforesaid meaning, and $R_3$ represents

with a compound of the formula $R_7X$, $R_7$ being alkyl, alkenyl, alkynyl, cycloalkyl, dialkylaminoalkyl or aralkyl as defined above and X is a halogen atom such as chlorine, bromine or iodine, for example methyl iodide, allyl bromide, benzyl bromide and diethylaminoethyl chloride, or with a compound of the formula $(R_7)_2SO_4$ in which $R_7$ stands for an alkyl radical as defined above, for example $(CH_3)_2SO_4$. The reaction is carried out according to known methods in the presence of a base, for example, an anhydrous alkali metal carbonate, such as potassium carbonate. The reaction is suitably carried out in the presence of a dry solvent, for example a ketone, such as acetone, or an aromatic hydrocarbon such as benzene. To accelerate or complete the reaction, the reaction mixture can be heated up to the boiling temperature of the solvent used.

Compounds of formula III in which $R_1$, $R_2$ and $R_4$ have the aforesaid meaning and $R_3$ stands for

wherein $R_7$ is a dialkylaminoalkyl group can be transformed into their acid addition salts by known methods, for example simply by adjusting the pH of a solution of the said compound with an acid to approximately neutral. Suitable acids are, for example, hydrochloric acid, hydrobromic acid, hydroiodic acid, sulfuric acid, phosphoric acid, acetic acid, oxalic acid, tartaric acid, citric acid, maleic acid and fumaric acid.

In the case of $R_7$ being an acyl group as defined above, the compound of formula III can be treated with an acid anhydride, for example formic-acetic anhydride, acetic anhydride, trifluoroacetic anhydride, propionic anhydride, or butyric anhydride, or with an acyl halide wherein acyl has the aforesaid meaning and the halogen is chlorine or bromine, for example α-bromoisobutyryl bromide, in the presence of a base such as a nitrogen-containing compound, for example pyridine, by a known method at a temperature in the range of from room temperature to 0° C.

In the case of $R_7$ being an alkoxycarbonyl group, the compound of formula III can be treated with a halocarbonic acid ester, preferably chlorocarbonic acid ethyl ester, or a dialkylcarbonic anhydride, in the presence of a base and in known manner.

When $R_7$ is an arylaminocarbonyl group, the compound of formula III can be treated with an organic isocyanate, for example phenyl isocyanate, according to a known method. The reaction can be carried out in the presence of a dry solvent, for example benzene or toluene. It can be accelerated or completed by heating, for example up to the boiling temperature of the solvent used.

It is another object of the present invention to provide a process for preparing compounds of formula III in which $R_2$ and $R_4$ are oxygen or

$R_6$ having the aforesaid meaning, with the exception that is does not stand for hydrogen, and $R_1$ and $R_3$ are

$R_7$ having the aforesaid meaning, which comprises treating compounds of the formulae II a, II b or other compounds of formula III in which $R_2$ and $R_4$ have the same meaning as defined above and $R_1$ and $R_3$ are

with a reagent as defined above depending on the nature of $R_7$. Some of the reactions can be facilitated by adding one of the described bases. By heating, for example up to the boiling temperature of the solvent used, the reactions can be accelerated or completed.

It is still another object of the invention to provide a process for preparing compounds of formula III in which $R_1$ and $R_4$ have the aforesaid meaning, $R_2$ is

with $R_6$ being an acyl group and $R_3$ is

which comprises treating with a base the compound of formula II a or another compound of formula III in which $R_1$ and $R_4$ have the aforesaid meaning, $R_2$ is

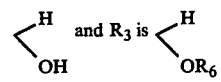

wherein $R_6$ is an acyl group. As base there can be used an alkali metal alkoxide, for example sodium methoxide or ethoxide. In this case the treatment can be carried out in the presence of a solvent, for example an ether, preferably dioxane, tetrahydrofuran or diethyl ether. The base can also be an alkali metal carbonate, for example sodium or potassium carbonate, or an alkali metal bicarbonate, for example potassium bicarbonate. In this case an alkanol having from 1 to 6 carbon atoms, for example methanol or ethanol, either with or without the addition of water, can be used as solvent. As base a basic metal oxide is suitable, for example basic alumina, which can be used in the presence of a solvent, for example an aromatic hydrocarbon such as benzene or toluene, an ether such as diethyl ether, dioxane or tetrahydrofuran. In all cases of a treatment with a base the reaction can be accelerated or completed by heating, for example up to the boiling point of the solvent used.

It is still another object of the invention to provide a process for preparing compounds of formula III in which $R_1$ is oxygen and $R_2$, $R_3$ and $R_4$ have the meanings defined above, with the exception that $R_3$ and $R_4$ cannot stand for

which comprises oxidizing by a known method the compound of formula II a or another compound of formula III wherein $R_1$ is

and $R_2$, $R_3$ and $R_4$ have the aforesaid meanings, for example with Jones reagent. The oxidation can be carried out in a solvent, for example a ketone such as acetone, at a temperature in the range of from room temperature to 0° C.

It is still another object of the invention to provide a process for preparing compounds of formula III in which $R_1$ and $R_2$ are oxygen and $R_3$ and $R_4$ have the meaning defined above, with the exception that they cannot stand for

which comprises oxidizing the compound of formula II a or another compound of formula III in which $R_1$ and $R_2$ are

and $R_3$ and $R_4$ have the aforesaid meaning by a known method using as oxidant, for example, Jones reagent, Collins reagent or Sarrett reagent.

It is still another object of the invention to provide a process for preparing compounds of formula III in which $R_1$, $R_2$ and $R_3$ have the same meaning as defined above, with the exception that they cannot stand for oxygen or

with $R_6$ being an acyl group, and $R_4$ is

which comprises reducing the compound of formula II a or II b or another compound of formula III in which $R_1$, $R_2$ and $R_3$ are as defined above and $R_4$ is oxygen by a known method using a complex metal hydride, for example lithium-aluminum hydride. The reaction can be carried out in the presence of a solvent, for example an ether such as a dialkyl ether, preferably diethyl ether, or a cyclic ether such as dioxane or tetrahydrofuran. The reaction can be carried out at a temperature below room temperature and down to 0° C.

According to another feature of the invention compounds of formula I in which $R_1$, $R_2$, $R_3$ and $R_4$ have the aforesaid meaning and $R_5$ is $-CH_2CH_3$ are prepared by catalytically hydrogenating a compound of formula II a or II b or another compound of formula I in which $R_1$, $R_2$, $R_3$ and $R_4$ have the indicated meaning and $R_5$ is $-CH=CH_2$, using as a catalyst metal, for example Raney nickel or a platinum metal, such as platinum, palladium, rhodium, and ruthenium, or the oxides and sulfides thereof. The platinum metal catalysts can be used in the form of the finely divided metals or supported on a carrier, such as asbestos, activated carbon, alumina, barium sulfate, or barium carbonate. The hydrogenation can be carried out in the presence of a solvent, for example an alkanol such as ethanol, an ether such as diethyl ether, a carboxylic acid, such as acetic acid, or an ester, such as ethyl acetate. The hydrogenation can be accelerated or completed by the application of pressure, for example up to 10 atmospheres, or heat, for example by heating to the boiling point of the solvent used.

The compounds of the invention are characterized by a very good hypotensive effect. Moreover, they have a vasodilating effect on peripheral vessels and a positive inotropic acitivity.

Owing to their hypotensive effect the compounds can be used in the treatment of heart and circulatory diseases, for example essential and malignant hypertonia, myovascular insufficiency, Angina pectoris, and disorders in the peripheral circulation. In theraphy, the compounds can be used in combination with other pharmacologically active substances, for example diuretics, antiarrhythmics, β-blockers, tranquillizers, coronary dilating substances, hypolipidemics and so on.

Owing to their positive inotropic activity, the compounds of the invention are suitable for the treatment of myovascular insufficiency, collapse due to hermorrhage and in the state of shock.

The compounds of the invention can be administered perorally or intravenously. Depending on the severity of the disease and the weight of the patient, the daily dose varies between 25 and 1,000 mg.

For peroral administration tablets or dragees containing 25 to 1,000 mg of active compound and the usual auxiliaries and carrier materials such as talcum, starch, lactose, are preferably used. For intravenous administration the active compound is dissolved or supended in a pharmaceutically tolerated plant oil, for example peanut oil or sesame oil, or it is dissolved in an alcohol such as ethanol, propanediol, glycerol or a mixture thereof.

The following examples illustrate the invention. The compound number refer to the table.

EXAMPLE 1

A mixture of 1.4 g of compound IIa or compound IIb and 200 mg of sodium hydroxide in 100 ml of 80% aqueous methanol was stirred at room temperature for 1 hour. The solvent was distilled, the residue diluted with water and the suspension extracted with chloroform. The chloroform extract was dried and the solvent removed under reduced pressure. The residue was recrystallized from ethyl acetate-petroleum ether (b.p. 60–80°) to give colorless crystals of compound 1, m.p. 176–178° C.

Compound 1 could be prepared also from compound IIa or compound IIb (in 80% aqueous methanol) by a treatment with aqueous hydrochloric acid (1:1). The reaction was complete after 24 hours.

Compound 2 was prepared in analogous manner.

EXAMPLE 2

A mixture of 4.92 g of compound IIb, 2.28 ml of dimethyl sulfate, and 30.0 g of anhydrous $K_2CO_3$ in 150 ml of dry acetone was refluxed for 6 hours and worked up according to conventional procedures. The product was crystallized from ethyl acetate — petroleum ether (bp. 60–80°) to give colorless crystals of compound 3, m.p. 195–197° C. Compound 4 was prepared in analogous manner. For the preparation of compound 5, the reaction time was increased to 18 hours.

EXAMPLE 3

A mixture of 5.0 g of compound IIa, 8.0 ml of benzyl bromide, 8.0 g of anhydrous KI and 25.0 g of anhydrous $K_2CO_3$ in 150 ml of dry acetone was refluxed for 17 hours and then filtered. The filtrate was evaporated to dryness under reduced pressure and the residue was purified by column chromatography over silica gel (200 g). The elution was done with petroleum ether (bp. 60–80°) followed by increasing proportions of benzene in petroleum ether, and then with benzene. The product was crystallized from petroleum ether (bp. 60–80°) to give crystals of compound 6, m.p. 132–134° C.

Compound 7 was prepared in analogous manner. Compound 8 was prepared by adjusting the pH of a solution of compound 7 in methanol to 7 by the addition of a solution of methanolic hydrochloric acid, and evaporating the solution to dryness.

EXAMPLE 4

To 5.0 g of compound IIb in 25.0 ml of pyridine, 25.0 ml of acetic anhydride were added and the reaction mixture was stirred for 3 hours at 0° and for 30 min at room temperature. The mixture was worked up according to conventional procedure. The crude residue was purified by column chromatography over silica gel and crystallization from ethyl acetate - petroleum ether (bp. 60-80°) to give colorless crystals of compound 10, m.p. 297-299° C.

Compounds 9 and 11-16 were prepared by slightly modifying the above process. Compound IIa was prepared from compound 1 using this procedure.

For the preparation of compounds 17-20 the reaction time was increased to 18 hours.

EXAMPLE 5

To a solution of 5.0 g of compound 1 in 700 ml of dry benzene cooled to 0°, 50 ml of pyridine and 50 ml of ethyl chloroformate were added with stirring. The mixture was stirred at 0° for 30 min and at room temperature for 1.5 hours, and then poured on to a water-ice mixture. The product was extracted with ethyl acetate (2000 ml). The extract was washed with 2 N HCl (3 × 300 ml) and water (3 × 300 ml), dried and evaporated to dryness under reduced pressure. The residue was crystallized from ethyl acetate-petroleum ether (bp. 60-80°) to give colorless crystals of compound 21, m.p. 166-167° C.

Compound 22 was prepared in analogous manner.

EXAMPLE 6

A solution of 0.5 g of compound IIa and 0.35 g phenylisocyanate in 25 ml toluene was refluxed for 20 hours. The solvent was distilled in vacuo. The residue was treated with 30 ml water and extracted with chloroform. The combined chloroform extracts were washed with water, dried and distilled. The residue was crystallized from chloroform-petroleum ether (bp. 60-80°) to give colorless crystals of compound 23, m.p. 212-216° C.

Compound 24 was prepared in analogous manner.

EXAMPLE 7

To a solution of 5.0 g of compound IIa in 500 ml of dry benzene 75 g of basic alumina were added. The mixture was stirred for 120 hours and filtered. The alumina was washed with 2500 ml of ethyl acetate. The benzene filtrate and the ethyl acetate washings were combined and evaporated to dryness under reduced pressure. The residue crystallized from chloroform-petroleum ether (bp. 60-80°) to give colorless crystals of compound IIb, m.p. 207-211° C. Compound IIb was also prepared from compound IIa (in anhydrous dioxane solution) by a treatment with sodium methylate (0.5-1.0 molar equivalent). The reaction was complete in 0.5 hour.

Compound 25 was prepared in analogous manner.

EXAMPLE 8

To a cooled solution (0-5°) of 4.8 g of dihydro-compound IIa (prepared as described in Example 11) in acetone (400 ml) 5.0 ml of Jones' reagent were added and the mixture was stirred at 0-5° for 10 minutes. The excess of the reagent was decomposed by the addition of 80 ml of methanol. The solvents were removed in vacuo and water was added to the residue. The resulting precipitate was filtered, dried and crystallized from benzene-petroleum ether (bp. 60-80°) to give colorless crystals of compound 26, m.p. 228-233° C.

EXAMPLE 9

To a cooled solution (0-5°) of dihydrocompound IIa (5.0 g, in pyridine, chromium trioxide (5.25 g) was added and the mixture was stirred at room temperature for 1 hr. and left overnight. The reaction mixture was diluted with water and extracted repeatedly with chloroform. The combined chloroform extracts were washed with water, dried and evaporated to dryness under reduced pressure. The residue was chromatographed over silica gel, and crystallized from petroleum ether (bp. 60-80°) to give colorless crystals of compound 27, m.p. 163-165° C.

EXAMPLE 10

To a solution of 5.0 g of compound IIa in 500 ml of dry ether cooled in an ice bath, 2.5 g of lithium aluminum hydride were slowly added with constant stirring. The mixture was refluxed for 4 hrs. The excess of reagent was decomposed by the addition of ethyl acetate. The reaction mixture was filtered. The organic layer was washed with water, dried and evaporated to dryness under reduced pressure. The product was crystallized from ethyl acetate-benzene to give crystals of compound 28, m.p. 204-209° C.

EXAMPLE 11

A mixture of compound IIa (5.4 g) and Pd/C (3.0 g) in ethyl acetate (150 ml) was stirred under an atmosphere of hydrogen for 2 hrs. at room temperature and at atmospheric pressure. The catalyst was filtered. The solution was evaporated to dryness and the residue was crystallized from ethyl acetate-petroleum ether (bp. 60-80°) to give colorless crystals of compound 29, m.p. 245-248° C.

What is claimed is:

1. A compound of the formula

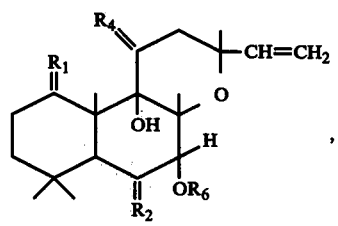

stereoisomers thereof, and acid addition salts of such a compound having a basic group, wherein $R_1$, $R_2$, $R_4$ are the same or different and are oxygen or

wherein $R_6$ is hydrogen, alkyl having up to 6 carbon atoms, dialkylaminoalkyl or phenalkyl in which the alkyl has at most 4 carbon atoms, benzoyl, alkanoyl having up to 10 carbon atoms, alkoxycarbonyl having from 2 to 10 carbon atoms, or phenylaminocarbonyl, excepting those two compounds in which, simultaneously, $R_4$ is oxygen, $R_1$ is

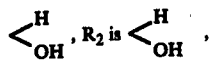, $R_2$ is , and $R_6$ is

or in which $R_4$ is oxygen, $R_1$ is

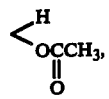

$R_2$ is and $R_6$ is hydrogen.

2. A compound as in claim 1 which is 8,13-epoxy-1,6,7,9-tetrahydroxy-labd-14-en-11-one.

3. A compound as in claim 1 which is 8,13-epoxy-7-formyloxy-1,6,9-trihydroxy-labd-14-en-11-one.

4. A compound as in claim 1 which is 6,7-diacetoxy-1,9-dihydroxy-8,13-epoxy-labd-14-en-11-one.

5. A compound as in claim 1 which is 8,13-epoxy-6-propionyloxy-1,7,9-trihydroxy-labd-14-en-11-one.

6. A pharmaceutical composition for the treatment of heart and circulatory disease which comprises an effective amount of a compound as in claim 1 in combination with a pharmaceutically acceptable carrier.

7. A method for the treatment of heart and circulatory disease which comprises administering to a patient suffering therefrom an effective amount of a compound as in claim 1.

* * * * *